United States Patent [19]

Honma et al.

[11] Patent Number: 5,183,539

[45] Date of Patent: Feb. 2, 1993

[54] METHOD OF PURIFYING CRUDE GLYCIDYL (METH)ACRYLATE

[75] Inventors: Akihiro Honma; Masahiro Kurokawa, both of Hiratsuka, Japan

[73] Assignee: Mitsubishi Gas Chemical Company, Inc., Tokyo, Japan

[21] Appl. No.: 793,958

[22] Filed: Nov. 15, 1991

[30] Foreign Application Priority Data

Nov. 21, 1990 [JP] Japan .................................. 2-314305

[51] Int. Cl.$^5$ ...................... B01D 3/34; C07D 301/36
[52] U.S. Cl. .......................................... 203/38; 203/49; 203/DIG. 6; 203/DIG. 21; 549/202; 549/515
[58] Field of Search .......... 203/49, 91, 38.6, DIG. 21, 203/DIG. 6; 549/515, 557, 202

[56] References Cited

U.S. PATENT DOCUMENTS

| | | | |
|---|---|---|---|
| 4,199,410 | 4/1980 | Ohrui et al. | 203/DIG. 21 |
| 4,210,493 | 7/1980 | Stewart et al. | 203/DIG. 21 |
| 4,260,821 | 4/1981 | Benjamin | 203/DIG. 21 |
| 4,755,262 | 7/1988 | Matsunaga et al. | 203/34 |

FOREIGN PATENT DOCUMENTS 0233843  8/1987  European Pat. Off. .
2113222  8/1983  United Kingdom .

OTHER PUBLICATIONS

English Abstract of Japanese Laid-Open Publication No. 255,273/1988.
English Abstract of Japanese Laid-Open Publication No. 124,777/1983.
English Abstract of Japanese Laid-Open Publication No. 42,075/1982.
Sakai et al., Chemical Abstracts 88:50369q (1978).

Primary Examiner—Virginia Manoharan
Attorney, Agent, or Firm—Wenderoth, Lind & Ponack

[57] ABSTRACT

A method of purifying a crude glycidyl (meth)acrylate, by (1) subjecting a crude glycidyl (meth)acrylate containing epichlorohydrin and other chlorine compounds as impurities to a stripping treatment with a mixed gas containing oxygen gas in the presence of a quaternary ammonium salt, and then (2) distilling the treated product to obtain a purified glycidyl (meth)acrylate.

5 Claims, No Drawings

METHOD OF PURIFYING CRUDE GLYCIDYL (METH)ACRYLATE

DETAILED DESCRIPTION OF THE INVENTION

The present invention relates to a method of purifying a crude glycidyl (meth)acrylate. More specifically, it relates to a method of purifying a crude glycidyl (meth)acrylate containing epichlorohydrin and other chlorine compounds.

Glycidyl acrylate and glycidyl methacrylate (to be generally called "glycidyl (meth)acrylate" hereinafter) are widely used in various fields of resins, thermosetting coating compositions, adhesives, fiber treating agents, antistatic agents, ion-exchange resins, and the like.

In recent years, a glycidyl (meth)acrylate of which the chlorine content is small is particularly desired in the fields of electronic materials and fibers.

In general, glycidyl (meth)acrylate is produced by reacting (meth)acrylic acid with epichlorohydrin to form chlorohydrin (meth)acrylate and dehydrochlorinating the chlorohydrin (meth)acrylate.

The above-obtained glycidyl (meth)acrylate generally contains residual chlorine compounds in a chlorine concentration of approximately 1,000 to 10,000 ppm. In the fields of electronic materials and fibers, the above residual chlorine compounds cause problems of a decrease in electric characteristics and a rash on the skin, and in recent years, it particularly has turned into an issue with regard to its carsinogenesis.

Further, when glycidyl (meth)acrylate is used in a resin and a coating composition, impurities of the above chlorine compounds also cause a decrease in performance.

It is therefore desirable to remove impurities of chlorine compounds from a produced glycidyl (meth)acrylate as much as possible.

In order to remove the chlorine compounds from glycidyl (meth)acrylate, it is general practice to employ a method in which glycidyl (meth)acrylate obtained by the reaction is subjected to redistillation.

Japanese Laid-Open Patent Publication No. 255,273/1988 discloses a method in which a hetero-poly acid or an alkali metal salt thereof is added to glycidyl (meth)acrylate and the resultant mixture is distilled, whereby the epichlorohydrin content can be reduced to 100 ppm or less.

In this method, however, the lowest content of the residual epichlorohydrin is 21 ppm, or it cannot be said that the removal of epichlorohydrin is satisfactory. Further, the above Japanese Laid-Open Patent Publication describes nothing with regard to the removal of chlorine compounds as a by-product other than epichlorohydrin.

Having regard to a process for producing a glycidyl group-containing compound containing no epichlorohydrin, Japanese Laid-Open Patent Publication No. 124,777/1983 discloses a method of removing epichlorohydrin in a multi-stage stripper optionally in the presence of an inert gas such as nitrogen gas.

However, when glycidyl (meth)acrylate, which has an unsaturated bond, is heated in a nitrogen gas atmosphere, the polymerization reaction sometimes proceeds even if the glycidyl (meth)acrylate contains a polymerization inhibitor. There is therefore a large risk of the above method causing a problem in practical use.

Furthermore, the above method is concerned only with the removal of epichlorohydrin, and the above Japanese Publication does not make any mention of the removal of other impurities of chlorine compounds.

Japanese Patent Publication No. 42,075/1982 discloses a method of purifying a crude glycidyl (meth)acrylate, in which the crude glycidyl (meth)acrylate is distilled together with an additional alkali metal salt of benzoic acid or a phenol having 1 to 3 nitro groups.

The above distillation method is characterized in that crude glycidyl (meth)acrylate can be purified without forming any polymer as a by-product. However, the above Japanese Patent Publication describes nothing with regard to the removal of by-products of chlorine compounds.

It is an object of the present invention to provide a method of purifying a crude glycidyl (meth)acrylate.

It is another object of the present invention to provide a method of purifying a crude glycidyl (meth)acrylate containing epichlorohydrin and other chlorine compounds.

It is further another object of the present invention to provide a method of purifying a crude glycidyl (meth)acrylate, in which the prior art problems can be overcome, and a high-purity glycidyl (meth)acrylate can be formed by efficiently removing impurities of epichlorohydrin and other chlorine compounds contained in the crude glycidyl (meth)acrylate without decreasing the yield of the high-purity glycidyl (meth)acrylate as a product in the purification step.

The other objects and advantages of the present invention will be apparent from the following description.

According to the present invention, the above objects and advantages of the present invention are achieved by a method of purifying a crude glycidyl (meth)acrylate, which comprises:

(1) subjecting a crude glycidyl (meth)acrylate containing epichlorohydrin and other chlorine compounds as impurities to a stripping treatment with a mixed gas containing oxygen gas in the presence of a quaternary ammonium salt, and then (2) distilling the treated product to obtain a purified glycidyl (meth)acrylate.

According to the purification method provided by the present invention, a crude glycidyl (meth)acrylate containing chlorine compounds in a chlorine concentration of about 1,000 to about 10,000 ppm can be converted to a purified glycidyl (meth)acrylate of which the chlorine concentration is reduced substantially to a concentration of hundreds ppm or lower, or further reduced to a concentration of tens ppm or lower.

The crude glycidyl (meth)acrylate used in the above step (1) of the present invention contains epichlorohydrin and other chlorine compounds. Such a crude glycidyl (meth)acrylate is obtained by a process known per se, for example, a process in which epichlorohydrin and a (meth)acrylic acid are allowed to react to form chlorohydrin (meth)acrylate and then, the resultant chlorohydrin (meth)acrylate is dehydrochlorinated.

Epichlorohydrin as an impurity contained in a crude glycidyl (meth)acrylate is derived from an unreacted starting material in many cases. Further, typical examples of other chlorine compounds are 1,3-dichloro-2-propanol, 2,3-dichloro-1-propanol, glycerin monochlorohydrin, 2-hydroxy-3-chloropropyl (meth)acrylate and 3-hydroxy-2-chloropropyl (meth)acrylate.

The quaternary ammonium salt used in the step (1) is selected, for example, from tetramethylammonium chloride, tetraethylammonium chloride, tetrabutylammonium chloride, triethylbenzylammonium chloride, trimethylbenzylammonium chloride, tetramethylammonium bromide, tetraethylammonium bromide and choline chloride.

The above quaternary ammonium salts may be used alone or in combination of two or more. Preferred among these are tetraethylammonium chloride, triethylbenzylammonium chloride and trimethylbenzylammonium chloride.

The amount of the quaternary ammonium salt for use per 100 parts by weight of the crude glycidyl (meth)acrylate is preferably 0.01 to 10 parts by weight, more preferably 0.1 to 5 parts by weight, particularly preferably 0.1 to 2 parts by weight.

In the conventional purification methods disclosed so far, it is impossible to remove chlorine compounds such as 1,3-dichloro-2-propanol, 2,3-dichloro-1-propanol, etc., contained as impurities in a product, since the vapor pressure of these chlorine compounds is very near to the vapor pressure of glycidyl (meth)acrylate.

However, when a crude glycidyl (meth)acrylate is purified in the presence of a quaternary ammonium salt as described above, chlorine compounds such as 1,3-dichloro-2-propanol, 2,3-dichloro-1-propanol, glycerin monochlorohydrin, etc., contained as impurities can be decomposed to epichlorohydrin, glycidol, and hydrochloric acid due to the catalytic activity of the quaternary ammonium salt in the step (1). Further, these decomposed impurities can be efficiently removed by a stripping treatment.

In the stripping treatment in the step (1) in the present invention, further, a mixed gas containing oxygen gas is used.

The mixed gas is a mixture of oxygen gas with any one of inert gases such as nitrogen gas, helium gas, argon gas and carbon dioxide gas.

The above inert gas may be used alone or in combination of two or more. Of these inert gases, nitrogen gas is preferred.

In the mixing ratio of oxygen gas and an inert gas, the oxygen concentration in the mixed gas is preferably 1 to 21% by volume, more preferably 5 to 21% by volume, particularly preferably 8 to 21% by volume.

Due to the use of a mixed gas having the above oxygen concentration, the polymerization of glycidyl (meth)acrylate can be inhibited, and impurities such as epichlorohydrin and other chlorine compounds can be efficiently removed without causing a decrease in the product yield.

In the stripping treatment in the step (1) of the present invention, the mixed gas is used in such an amount that the flow rate of the mixed gas per kg of glycidyl (meth)acrylate at 20° C. under atmospheric pressure is preferably 0.1 to 500 ml/minute, more preferably 0.5 to 100 ml/minute, particularly preferably 1 to 50 ml/minute.

When the gas flow rate is less than 0.1 ml/minute, the purification is liable to be insufficient. When it is more than 500 ml/minute, the product yield is liable to decrease.

When a crude glycidyl (meth)acrylate is subjected to the stripping treatment in the presence of a quaternary ammonium salt, the crude glycidyl (meth)acrylate liquid is brought into contact with the mixed gas as follows. For example, there is available a method in which the mixed gas is blown into the crude glycidyl (meth)acrylate liquid while the liquid is stirred, or in which the mixed gas is brought into contact with a thin film of the crude glycidyl (meth)acrylate which is being formed with a film evaporator.

When the purification is carried out by blowing the mixed gas into the crude glycidyl (meth)acrylate liquid under stirring, the liquid may be stirred with a stirring blade or by circulating it with a rotor such as a pump.

When the mixed gas is blown into the crude glycidyl (meth)acrylate liquid containing a quaternary ammonium salt, an insufficient stirring may result in an insufficient removal of epichlorohydrin and other chlorine compounds.

Gas discharged out of the system is cooled through a heat exchanger and recovered as liquid impurities, or treated as a waste liquid.

The above stripping treatment is carried out under atmospheric pressure or under reduced pressure, preferably under reduced pressure.

The pressure for the stripping treatment is in the range of 1 to 500 mmHg, particularly preferably 2 to 50 mmHg. Under the above pressure range, the stripping treatment can be carried out efficiently and without any decrease in product yields.

When the stripping treatment in the step (1) of the present invention is carried out at a pressure, e.g., higher than atmospheric pressure, the relatively high temperature must be chosen. Under such temperature conditions, disadvantages such as polymerization of crude glycidyl (meth)acrylate are liable to take place, which is undesirable.

The temperature for the above stripping treatment is not higher than the boiling point of a crude glycidyl (meth)acrylate and not lower than the boiling point of epichlorohydrin.

When the stripping treatment is carried out at a temperature not higher than the boiling point of a crude glycidyl (meth)acrylate containing a quaternary ammonium salt, there is an effect that the yield of glycidyl (meth)acrylate increases. When the purification is carried out at a temperature not lower than the boiling point of epichlorohydrin, epichlorohydrin and other chlorine compounds can be efficiently removed for a short time.

In the step (2) of the present invention, the crude glycidyl (meth)acrylate from which low-boiling chlorine compounds have been removed in the stripping treatment in the step (1) is distilled.

In this step (2), the quaternary ammonium salt and a high-boiling chlorine compounds are further removed.

The distillation is preferably carried out under reduced pressure. By the distillation, a purified glycidyl (meth)acrylate can be obtained.

Although depending upon the initial concentration of chlorine compounds, the content, as a chlorine concentration, of the chlorine compounds in the above-purified glycidyl (meth)acrylate is from hundreds ppm to 50 ppm or lower.

The present invention will be more specifically described hereinafter by reference to Examples and Comparative Example.

The measurements described in Examples were carried out as follows.

(a) Starting materials and products were measured for their purities according to the GC method.
(b) Starting materials and products were analyzed for their chlorine concentrations as follows.

A sample (0.5 g) was dissolved in about 20 ml of a 0.1N KOH/methanol solution in a 100 ml conical flask, and the resultant sample solution was heated in a constant-temperature chamber having a cooling tube at 70° C.

After 15 minutes, the sample solution was cooled with cold water and washed into a 100 ml beaker, and 1 ml of 30% nitric acid was added to the sample solution to acidify it. Then, the sample solution was subjected to potentiometric titration with a 1/1,000N silver nitrate solution.

In addition, a blank experiment using a solution containing no sample was carried out, and the resultant titration value was deducted from a titration value obtained above to determine the chlorine concentration of the sample.

In Examples and Comparative Examples, all the purities (%) of starting materials and products stand for % by weight, and values having a ppm unit are based on weight.

EXAMPLE 1

(1) A ten-liter four-necked flask was charged with 5.66 kg of epichlorohydrin, 662 g of sodium carbonate anhydride and 10.0 g of hydroquinone monomethyl ether, and the mixture was heated.

When the temperature of the contents in the flask reached 105.5° C., 861 g of methacrylic acid was added dropwise through a dropping funnel over 3 hours.

During the addition, the temperature of the contents was under control to keep it between 105° C. and 107° C.

Epichlorohydrin and water were azeotropically distilled and removed out of the system soon after the above addition was started, and the epichlorohydrin was recycled to the reaction system.

About one hour after the addition was finished, the temperature was found to have increased up to 114° C., and almost no azeotropic distillation occurred.

Then, 2.4 g of tetramethylammonium chloride as a catalyst was added, and the contents were allowed to react at the above temperature for 2 hours.

After the reaction, the reaction mixture was cooled to 20° C., 2.5 kg of water was added, and the resultant mixture was stirred for 10 minutes.

The mixture was allowed to stand for 2 hours to be separated into an oil layer and a water layer.

Epichlorohydrin was recovered from the oil layer by distillation under reduced pressure, and the distillation was further carried out under an absolute pressure between 1 mmHg and 2 mmHg to give a crude glycidyl methacrylate in an amount corresponding to 87.8% of the stoichiometric yield.

The above crude glycidyl methacrylate had a purity of 98.0%, and it contained 0.65% of epichlorohydrin, 0.52% of 1,3-dichloro-2-propanol, 0.22% of 2,3-dichloro-1-propanol, 0.005% of glycerin monochlorohydrin and 0.36% of 2-hydroxy-3-chloropropyl methacrylate. The chlorine concentration of the above crude glycidyl methacrylate was 7,800 ppm.

(2) A one-liter five-necked flask having a distillation column, a gas-introducing tube, a thermometer, a stirrer and a gas discharge tube with a trap was charged with 400 g of the crude glycidyl methacrylate having a purity 98.0% and a chlorine concentration of 7,800 ppm, obtained in the above (1), 4.65 g of tetraethylammonium chloride and 0.16 g of p-methoxyphenol. Then, the crude glycidyl methacrylate was subjected to a stripping treatment by blowing air into the resultant liquid (flow rate at 20° C. under atmospheric pressure: 10 ml/min.) for 6 hours while the liquid temperature was kept between 67° C. and 68° C. under an absolute pressure of 4 to 5 mmHg.

After the stripping treatment was carried out for 6 hours, the crude glycidyl methacrylate was purified by distillation under an absolute pressure of 3 to 4 mmHg at a column top temperature between 57° C. and 60° C.

The amounts of the resultant fractions were as follows: an initial distillate 20.0 g, a main distillate 306.8 g, a still-bottom product 75.5 g, and a trap 1.1 g.

In the above purification, the yield of the product [main distillate: glycidyl methacrylate] was 76.7% by weight. The chlorine concentration of the product was 90 ppm.

EXAMPLE 2

(1) A vacuum line was set at the same apparatus as that used in Example 1 (1) so that the pressure in the reaction system was allowed to be reduced. Then, the flask was charged with 5.7 kg of epichlorohydrin, 583 g of sodium carbonate anhydride and 4.3 g of phenothiazine, and the flask was immersed in an oil bath at 90° C. At the same time the pressure in the flask was reduced to an absolute pressure of 650 to 700 mmHg, and 861 g of methacrylic acid was added dropwise over 3 hours. During the addition, the temperature of the contents in the flask was between 80° C. and 84° C.

After the addition was stirred, azeotropically distilled water was removed out of the system, and azeotropically distilled epichlorohydrin was recycled to the reaction system.

Thirty minutes after the addition was finished, the reaction system was returned to atmospheric pressure, the temperature of the oil bath was increased to 120° C., and water was further distilled off under atmospheric pressure.

When the internal temperature of the flask became 114° C., 4.8 g of triethylbenzylammonium chloride as a catalyst was added. The internal temperature was lowered to 105° C., and the contents were allowed to react for 3 hours.

After the reaction, the reaction mixture was cooled to 25° C., 2.75 kg of water was added, and the mixture was stirred for 10 minutes.

The reaction mixture was allowed to stand for 1.5 hours to separate it into an oil layer and a water layer.

The oil layer was distilled under reduced pressure in the same manner as in Example 1 (1) to give a crude glycidyl methacrylate in an amount corresponding to 90.2% of the stoichiometric yield.

The above crude glycidyl methacrylate had a purity of 98.3%, and it contained 0.35% of epichlorohydrin, 0.32% of 1,3-dichloro-2-propanol, 0.13% of 2,3-dichloro-1-propanol, 0.005% of glycerin monochlorohydrin and 0.26% of 2-hydroxy-3-chloropropyl methacrylate. The chlorine concentration of the above crude glycidyl methacrylate was 4,600 ppm.

(2) The same apparatus as that used in Example 1 (2) was charged with 400 g of the crude glycidyl methacrylate having a purity of 98.3% and a chlorine concentration of 4,600 ppm, obtained in the above (1), 3.1 g of tetramethylammonium chloride and 0.16 g of p-methoxyphenol. Then, the crude glycidyl methacrylate was subjected to a stripping treatment by blowing an oxygen/nitrogen mixed gas containing 10% by volume of oxygen gas into the resultant liquid (flow rate at 20° C. under atmospheric pressure: 5 ml/min.) for 6 hours while the liquid temperature was kept between 67° C. and 68° C. under an absolute pressure of 4 mmHg.

Thereafter, the crude glycidyl methacrylate was purified by distillation under an absolute pressure of 3 to 4 mmHg at a column top temperature between 57° C. and 60° C.

The amounts of the resultant fractions were as follows: an initial distillate 3.0 g, a main distillate 285.0 g, a still-bottom product 100.3 g, and a trap 0.9 g.

In the above purification, the yield of the product (main distillate: glycidyl methacrylate) was 71.3% by weight. The chlorine concentration of the product was 420 ppm.

EXAMPLE 3

The same apparatus as that used in Example 1 (2) was charged with 400 g of the same crude glycidyl methacrylate having a purity of 98.0% and a chlorine concentration of 7,800 ppm as that obtained in Example 1 (1), 2.0 g of triethylbenzylammonium chloride and 0.20 g of p-methoxyphenol. Then, the crude glycidyl methacrylate was subjected to a stripping treatment by blowing an oxygen/nitrogen mixed gas containing 8% by volume of oxygen gas into the resultant liquid (flow rate at 20° C. under atmospheric pressure: 15 ml/min.) for 6 hours while the liquid temperature was kept between 68° C. and 70° C. under an absolute pressure of 5 mmHg.

Thereafter, the crude glycidyl methacrylate was purified by distillation under an absolute pressure of 3 to 4 mmHg at a column top temperature between 57° C. and 60° C.

The amounts of the resultant fractions were as follows: an initial distillate 15.3 g, a main distillate 290.5 g, a still-bottom product 104.4 g, and a trap 1.1 g.

In the above purification, the yield of the product (main distillate: glycidyl methacrylate) was 70.1% by weight. The chlorine concentration of the product was 180 ppm.

EXAMPLE 4

The same apparatus as that used in Example 1(2) was charged with 800 g of the same crude glycidyl methacrylate having a purity of 98.3% and a chlorine concentration of 4,600 ppm as that obtained in Example 2(1), 1.0 g of trimethylbenzylammonium chloride and 2.0 g of p-methoxyphenol. Then, the absolute pressure in the flask was reduced to 5 mmHg, and the crude glycidyl methacrylate was subjected to a stripping treatment by blowing air into the crude glycidyl methacrylate liquid at a rate of 3 ml/minute and keeping the temperature inside the flask between 66.1° C. and 66.7° C. for 8 hours.

Thereafter, the purification by distillation under reduced pressure was carried out in the same conditions as in Examples 1 to 3.

The amount of the resultant main distillate (glycidyl methacrylate) was 541.8 g, and the purity of the glycidyl methacrylate was improved up to 99.1%.

In the above purification, the yield of the product (glycidyl methacrylate) was 67.7% by weight, and the chlorine concentration of the product was 130 ppm.

COMPARATIVE EXAMPLE 1

The same apparatus as that used in Example 1(2) was charged with 400 g of the same glycidyl methacrylate having a purity of 98.0% and a chlorine concentration of 7,800 ppm as that obtained in Example 1(1) and 2.0 g of p-methoxyphenol. Then, the absolute pressure in the flask was reduced to 10 mmHg, and the resultant liquid was distilled while a nitrogen gas was blown into the liquid at a rate of 1 ml/minute. An initial distillate in an amount of 27 g (6.8% by weight of the charged amount) was removed, and 131 g of a main distillation fraction was obtained (product yield: 32.6% by weight).

The chlorine concentration of the main distillation fraction was 2,800 ppm.

What is claimed is:
1. A method of purifying a crude glycidyl acrylate or a crude glycidyl methacrylate, which comprises:
   (1) subjecting a crude glycidyl acrylate or a crude glycidyl methacrylate containing, as impurities, epichlorohydrin and other chlorine compounds selected from the group consisting of 1,3-dichloro-2-propanol, 2,3-dichloro-1-propanol, glycerin monochlorohydrin, 2-hydroxy-3-chloropropyl acrylate, 2-hydroxy-3-chloropropyl methacrylate, 3-hydroxy-2-chloropropyl acrylate and 3-hydroxy-2-chloropropyl methacrylate to a stripping treatment with a mixed gas containing oxygen gas in the presence of a quaternary ammonium salt, and then
   (2) distilling the treated product to obtain a purified glycidyl acrylate or a purified glycidyl methacrylate,
   wherein the mixed gas is used at a flow rate of 0.1 to 500 ml/minute, as a flow rate at 20° C. under atmospheric pressure, per kilogram of the crude glycidyl acrylate or methacrylate.

2. The method of claim 1, wherein the quaternary ammonium salt is at least one member selected from the group consisting of tetramethylammonium chloride, tetraethylammonium chloride, triethylbenzylammonium chloride and trimethylbenzylammonium chloride.

3. The method of claim 1, wherein the quaternary ammonium salt is used in an amount of 0.01 to 10 parts by weight per 100 parts by weight of the crude glycidyl acrylate or methacrylate.

4. The method of claim 1, wherein the mixed gas used in the stripping treatment contains a nitrogen gas and an oxygen gas, the amount of the oxygen gas being 1 to 21% by volume.

5. The method of claim 1, wherein the crude glycidyl acrylate or methacrylate is a product obtained by dehydrochlorination of chlorohydrin acrylate or methacrylate formed by a reaction between epichlorohydrin and acrylic or methacrylic acid.

* * * * *

REEXAMINATION CERTIFICATE (3120th)

United States Patent [19]

Honma et al.

[11] B1 5,183,539

[45] Certificate Issued Feb. 4, 1997

[54] METHOD OF PURIFYING CRUDE GLYCIDYL (METH)ACRYLATE

[75] Inventors: Akihiro Honma; Masahiro Kurokawa, both of Hiratsuka, Japan

[73] Assignee: Mitsubishi Gas Chemical Company, Inc., Tokyo, Japan

Reexamination Request:
No. 90/003,685, Jan. 11, 1995

Reexamination Certificate for:
Patent No.: 5,183,539
Issued: Feb. 2, 1993
Appl. No.: 793,958
Filed: Nov. 15, 1991

[30] Foreign Application Priority Data

Nov. 21, 1990 [JP] Japan ................ 2-314305

[51] Int. Cl.$^6$ .............. B01D 3/34; C07D 301/36
[52] U.S. Cl. .............. 203/38; 203/49; 203/DIG. 6; 203/DIG. 21; 549/202; 549/515
[58] Field of Search ............ 203/38, 49, DIG. 6, 203/DIG. 21, 91; 549/515, 557, 202

[56] References Cited

U.S. PATENT DOCUMENTS

| | | | |
|---|---|---|---|
| 4,199,410 | 4/1980 | Ohrui et al. | 203/DIG. 21 |
| 4,210,493 | 7/1980 | Stewart et al. | 203/DIG. 21 |
| 4,260,821 | 4/1981 | Benjamin | 203/DIG. 21 |
| 4,755,262 | 7/1988 | Matsunaga et al. | 203/34 |
| 5,207,874 | 5/1993 | Hess et al. | 203/49 |
| 5,380,884 | 1/1995 | Hosokawa et al. | 549/515 |

FOREIGN PATENT DOCUMENTS

| | | |
|---|---|---|
| 0233843 | 8/1987 | European Pat. Off. |
| 48-36117 | 5/1973 | Japan . |
| 53-90213 | 8/1978 | Japan . |
| 56-8375 | 1/1981 | Japan . |
| 2113222 | 8/1983 | United Kingdom . |

OTHER PUBLICATIONS

PTO Complete Translation of Japanese Kokai Patent Application No. Sho 48 [1973]-36117; pp. 1-13 and Japanese Kokai Patent Publication No. 53-090213, pp. 1-5.
Sakai et al., Chemical Abstracts 88:50369q (1978).
English Abstract of Japanese Laid-Open Publication No. 255,273/1988.
English Abstract of Japanese Laid-Open Publication No. 124,777/1983.
English Abstract of Japanese Laid-Open Publication No. 42,075/1982.

*Primary Examiner*—Virginia Manoharan

[57] ABSTRACT

A method of purifying a crude glycidyl (meth)acrylate, by (1) subjecting a crude glycidyl (meth)acrylate containing epichlorohydrin and other chlorine compounds as impurities to a stripping treatment with a mixed gas containing oxygen gas in the presence of a quaternary ammonium salt, and then (2) distilling the treated product to obtain a purified glycidyl (meth)acrylate.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 5 is cancelled.

Claim 1 is determined to be patentable as amended.

Claims 2–4, dependent on an amended claim, are determined to be patentable.

New claims 6–7 are added and determined to be patentable.

1. A method of purifying a crude glycidyl acrylate or a crude glycidyl methacrylate, which comprises:

(1) subjecting a crude glycidyl acrylate or a crude glycidyl methacrylate containing, as impurities, epichlorohydrin and other chlorine compounds selected from the group consisting of 1,3-dichloro-2-propanol, 2,3-dichloro-1-propanol, glycerin monochlorohydrin, 2-hydroxy-3-chloropropyl acrylate, 2-hydroxy-3-chloropropyl methacrylate, 3-hydroxy-2-chloropropyl acrylate and 3-hydroxy-2-chloropropyl methacrylate, *having a total chlorine concentration of about 1000 to about 10,000 ppm*, to a stripping treatment with a mixed gas containing oxygen gas in the presence of a quaternary ammonium salt *to reduce the chlorine concentration in the crude glycidyl acrylate or crude glycidyl methacrylate*, and then (2) distilling the treated product *in which epichlorohydrin has been removed in step (1)* to obtain a purified glycidyl acrylate or a purified glycidyl methacrylate *of further reduced chlorine concentration*, wherein the mixed gas is used at a flow rate of 0.1 to 500 ml/minute, as a flow rate at 20° C. under atmospheric pressure, per kilogram of the crude glycidyl acrylate or methacrylate.

6. *The method of claim 1, wherein the crude glycidyl acrylate or methacrylate is a product obtained by a reaction between epichlorohydrin and sodium acrylate or methacrylate with a release of sodium halide.*

7. *The method of claim 1, wherein the 1,3-dichloro-2-propanol, 2,3-dichloro-1-propanol and glycerin monochlorohydrin as impurities are decomposed to epichlorohydrin, glycidol and hydrochloric acid in the step (1).*

* * * * *